US010814019B2

(12) United States Patent
Maki et al.

(10) Patent No.: US 10,814,019 B2
(45) Date of Patent: Oct. 27, 2020

(54) MRI SIGNAL SUPPRESSION AGENTS, COMPOSITIONS, AND METHODS

(71) Applicant: University of Washington, Seattle, WA (US)

(72) Inventors: Jeffrey Maki, Seattle, WA (US); Gregory J. Wilson, Seattle, WA (US)

(73) Assignee: University of Washington, Seattle, WA (US)

( * ) Notice: Subject to any disclaimer, the term of this patent is extended or adjusted under 35 U.S.C. 154(b) by 336 days.

(21) Appl. No.: 15/323,252

(22) PCT Filed: Jun. 30, 2015

(86) PCT No.: PCT/US2015/038588
§ 371 (c)(1),
(2) Date: Dec. 30, 2016

(87) PCT Pub. No.: WO2016/004061
PCT Pub. Date: Jan. 7, 2016

(65) Prior Publication Data
US 2017/0143853 A1 May 25, 2017

Related U.S. Application Data

(60) Provisional application No. 62/019,183, filed on Jun. 30, 2014.

(51) Int. Cl.
*A61K 49/00* (2006.01)
*A61K 49/10* (2006.01)
(Continued)

(52) U.S. Cl.
CPC ............ *A61K 49/103* (2013.01); *A61B 5/055* (2013.01); *A61B 5/418* (2013.01); *A61K 49/18* (2013.01);
(Continued)

(58) Field of Classification Search
CPC .......... G01R 33/20–64; G01R 33/5601; G01R 33/5602; G01R 33/50; G01R 33/5607; G01R 33/5635; A61K 49/06
See application file for complete search history.

(56) References Cited

U.S. PATENT DOCUMENTS 5,736,121 A * 4/1998 Unger ................ A61K 49/0419
424/9.32
5,855,868 A * 1/1999 Fahlvik ................ A61K 49/186
424/646

(Continued)

FOREIGN PATENT DOCUMENTS

WO           98/10798 A1    3/1998
WO        2006/099516 A2    9/2006
WO     WO-2015154007 A1 *  10/2015 ............. A61K 49/08

OTHER PUBLICATIONS

Jinnan Wang, "Enhanced Image Quality in Black-Blood MRI by Using the Improved Motion-Sensitized Driven-Equilibrium (iMSDE) Sequence", J Magn Reson Imaging. May 2010 ; 31(5): 1256-1263 (Year: 2010).*

(Continued)

*Primary Examiner* — Joanne M Hoffman
(74) *Attorney, Agent, or Firm* — Christensen O'Connor Johnson Kindness PLLC

(57) ABSTRACT

To solve the problem of differentiating veins from lymphatics in MRI images, among other uses, the disclosed embodiments relate to compositions, kits, systems, and methods that include an MRI contrast agent and an MRI suppression agent that is also a blood pool agent. Using appropriate MRI techniques, the MRI suppression agent will suppress signal in its location, while signal enhanced by the MRI contrast agent in other locations will not be suppressed. The result is a clarified MRI image with only non-vascular regions enhanced.

12 Claims, 7 Drawing Sheets

(51) Int. Cl.
| | |
|---|---|
| G01R 33/48 | (2006.01) |
| G01R 33/56 | (2006.01) |
| A61B 5/055 | (2006.01) |
| A61B 5/00 | (2006.01) |
| A61K 49/18 | (2006.01) |

(52) U.S. Cl.
CPC ...... *A61K 49/1863* (2013.01); *G01R 33/4828* (2013.01); *G01R 33/5601* (2013.01); *G01R 33/5607* (2013.01)

(56) References Cited

U.S. PATENT DOCUMENTS

| | | | |
|---|---|---|---|
| 7,082,326 B2 | 7/2006 | Johansson | |
| 8,840,868 B2 | 9/2014 | Thurman et al. | |
| 2002/0087071 A1* | 7/2002 | Schmitz | A61B 5/0263 600/420 |
| 2002/0168321 A1* | 11/2002 | Tournier | A61K 49/1806 424/9.32 |
| 2003/0120151 A1* | 6/2003 | Constantinides | A61K 49/126 600/431 |
| 2004/0189297 A1* | 9/2004 | Bock | G01R 33/5601 324/307 |
| 2005/0171424 A1* | 8/2005 | Brechbiel | A61K 49/0002 600/420 |
| 2007/0059775 A1* | 3/2007 | Hultman | A61K 41/0052 435/7.2 |
| 2007/0104650 A1 | 5/2007 | Cunningham et al. | |
| 2008/0194944 A1 | 8/2008 | Edelman | |
| 2008/0218169 A1* | 9/2008 | Bookwalter | G01R 33/4828 324/309 |
| 2009/0076374 A1* | 3/2009 | Kimura | A61B 5/055 600/410 |
| 2009/0155181 A1 | 6/2009 | Rowe | |
| 2009/0299172 A1* | 12/2009 | Corot | A61B 5/055 600/420 |
| 2009/0317327 A1* | 12/2009 | Pilgrimm | A61K 41/0052 424/1.89 |
| 2010/0016706 A1* | 1/2010 | Wohlgemuth | A61B 5/055 600/410 |
| 2010/0026298 A1* | 2/2010 | Wald | G01R 33/5616 324/309 |
| 2010/0172842 A1* | 7/2010 | Israeli | A61B 5/055 424/9.3 |
| 2010/0253342 A1* | 10/2010 | Kimura | A61B 5/0275 324/309 |
| 2010/0296714 A1* | 11/2010 | Schmainda | A61B 5/0263 382/131 |
| 2010/0303733 A1* | 12/2010 | Hyde | A61K 49/1818 424/9.341 |
| 2011/0104052 A1* | 5/2011 | Barnett | A61K 9/0019 424/1.21 |
| 2012/0003160 A1* | 1/2012 | Wolf | A61B 5/0515 424/9.32 |
| 2012/0101367 A1 | 4/2012 | Kim | |
| 2017/0273578 A1* | 9/2017 | Finn | A61B 5/055 |
| 2018/0028683 A1* | 2/2018 | Wong | A61K 41/0028 |

OTHER PUBLICATIONS

Zhuxian Zhou, "Gadolinium-Based Contrast Agents for MR Cancer Imaging", Wiley Interdiscip Rev Nanomed Nanobiotechnol. Jan. 2013 ; 5(1): 1-18 (Year: 2013).*
Goyen, "0.5 M Gd Chelate (Magnevistt) Versus 1.0 M Gd Chelate (Gadovistt): Dose-Independent Effect on Image Quality of Pelvic Three-Dimensional MR-Angiography", Journal of Magnetic Resonance Imaging 14:602-607 (2001) (Year: 2001).*
Sevick-Muraca, "Emerging lymphatic imaging technologies for mouse and man", J Clin Invest. 2014;124(3):905-914 (Year: 2014).*
Stabi, "Ferumoxytol Use as an Intravenous Contrast Agent for Magnetic Resonance Angiography", The Annals of Pharmaco therapy • Dec. 2011, vol. 45 (Year: 2011).*
Sena, "Magnetic resonance lymphangiography with a nano-sized gadolinium-labeled dendrimer in small and large animal models", Nanomedicine (Lond). Oct. 2010 ; 5(8): 1183-1191 (Year: 2010).*
Lu Q, Delproposto Z, Hu A, Tran C, Liu N, et al. (2012) MR Lymphography of Lymphatic Vessels in Lower Extremity with Gynecologic Oncology-Related Lymphedema. PLoS One 7(11): e50319. (Year: 2012).*
Rane, "Clinical Feasibility of Noninvasive Visualization of Lymphatic Flow using Principles of Spin Labeling MRI: Implications for Lymphedema Assessment", Radiology. Dec. 2013 ; 269(3): 893-902. (Year: 2013).*
Munn, "Imaging the lymphatic system", Microvasc Res. Nov. 2014 ; 0: 55-63. (Year: 2014).*
Lohrmann, "Interstitial MR lymphangiography—A diagnostic imaging method for the evaluation of patients with clinically advanced stages of lymphedema", Acta Tropica 104 (2007) 8-15 (Year: 2007).*
Lohrmann, "Assessment of the lymphatic system in patients with diffuse lymphangiomatosis by magnetic resonance imaging", European Journal of Radiology 80 (2011) 576-581 (Year: 2011).*
Kobayashi, "Micro-magnetic Resonance Lymphangiography in Mice Using a Novel Dendrimer-based Magnetic Resonance Imaging Contrast Agent", Cancer Research 63, 271-276, Jan. 15, 2003 (Year: 2003).*
International Preliminary Report on Patentability dated Jan. 3, 2017, issued in corresponding International Application No. PCT/US15/038588, filed Jun. 30, 2015, 7 pages.
International Search Report and Written Opinion dated Sep. 23, 2015, issued in corresponding International Application No. PCT/US15/038588, filed Jun. 30, 2015, 9 pages.
Balakrishnan, V.S., et al., "Physicochemical Properties of Ferumoxytol, A New Intravenous Iron Preparation," European Journal of Clinical Investigation 39:489-496, 2009.
Bashir, M.R., et al., "Retrospective Assessment of the Utility of an Iron-Based Agent for Contrast-Enhanced Magnetic Resonance Venography in Patients With Endstage Renal Diseases," Journal of Magnetic Resonance Imaging 40(1):113-118, 2013.
Bulte, J.W., et al., Frequency Dependence of MR Relaxation Times. II Iron Oxides, Journal of Magnetic Resonance Imaging 3:641-648, 1993.
Chang, D.W., et al., "A Prospective Analysis of 100 Consecutive Lymphovenous Bypass Cases for Treatment of Extremity Lymphedema," Plastic and Reconstructive Surgery 132:1305-1314, Nov. 2013.
Eggers, H., et al., "Dual-Echo Dixon Imaging With Flexible Choice of Echo Times," Magnetic Resonance in Medicine 65:96-107, 2011.
"FDA Drug Safety Communication: FDA strengthens warnings and changes prescribing instructions to decrease the risk of serious allergic reactions with anemia drug Feraheme (ferumoxytol)," Mar. 30, 2015, <http://www.fda.gov/Drugs/DrugSafety/ucm440138.htm> [retrieved Jun. 13, 2015], 4 pages.
Koshima, I., et al., "Long-Term Follow-Up After Lymphaticovenular Anastomosis for Lymphedema in the Leg," Journal of Reconstructive Microsurgery 19(4):209-215, 2003.
Landry, R., et al., "Pharmacokinetic Study of Ferumoxytol: A New Iron Replacement Therapy in Normal Subjects and Hemodialysis Patients," American Journal of Nephrology 25:400-410, 2005.
Li, W., et al., "First-Pass Contrast-Enhanced Magnetic Resonance Angiography in Humans Using Ferumoxytol, A Novel Ultrasmall Superparamagnetic Iron Oxide (USPIO)-Based Blood Pool Agent," Journal of Magnetic Resonance Imaging 21:46-52, 2004.
Lohrmann, C., et al., "High-Resolution MR Lymphangiography in Patients With Primary and Secondary Lymphedema," American Journal of Roentgenology 187:556-561, 2006.
Lohrmann, C., et al., "MR Lymphangiography for the Assessment of the Lymphatic System in Patients Undergoing Microsurgical Microsurgical Reconstructions of Lymphatic Vessels," Microvascular Research 76:42-45, 2008.
Maki, J.H., et al., "Dark Blood Magnetic Resonance Lymphangiography Using Dual-Agent Relaxivity Contrast (DARC-MRL): A Novel Method Combining Gadolinium and Iron Contrast Agents," Current Problems in Diagnostic Radiology 45:174-179, 2016.

(56) References Cited

OTHER PUBLICATIONS

Mitsumori, L.M., et al., "MR Lymphangiography: How I Do It," Journal of Magnetic Resonance Imaging 42(6):1465-1477, Dec. 2015.

Neuwelt, E.A., et al., "Ultrasmall Superparamagnetic Iron Oxides (USPIOs): A Future Alternative Magnetic Resonance (MR) Contrast Agent for Patients at Risk for Nephrogenic Systemic Fibrosis (NSF)?" Kidney International 75:465-474, 2008.

Notohamiprodjo, M., et al., "MR Lymphangiography at 3.0 T: Correlation With Lymphoscintigraphy," Radiology 264:78-87, 2012.

Notohamiprodjo, M., et al., "MR-Lymphangiography at 3.0 T—A Feasibility Study," European Radiology 19:2771-2778, 2009.

Olszewski, W.L., "Lymphovenous Microsurgical Shunts in Treatment of Lymphedema of Lower Limbs: A 45-Year Experience of One Surgeon/One Center," European Journal of Vascular and Endovascular Surgery 45(3):282-290, Mar. 2013.

Shah, C., and F.A. Vicini, "Breast Cancer-Related Arm Lymphedema: Incidence Rates, Diagnostic Techniques, Optimal Management and Risk Reduction Strategies," International Journal of Radiation Oncology Biology Physics 81(4):907-914, Nov. 2011.

Szuba, A., et al., "The Third Circulation: Radionuclide Lymphoscintigraphy in the Evaluation of Lymphedema," Journal of Nuclear Medicine 44:43-57, 2003.

Tiwari, P., et al., "Breast and Gynecologic Cancer-Related Extremity Lymphedema: A Review of Diagnostic Modalities and Management Options," World Journal of Surgical Oncology 11:237, 2013, 13 pages.

Williams, W.H., et al., "Radionuclide Lymphangioscintigraphy in the Evaluation of Peripheral Lymphedema," Clinical Nuclear Medicine 25(6):451-464, 2000.

\* cited by examiner

MRI SIGNAL SUPPRESSION AGENTS, COMPOSITIONS, AND METHODS

CROSS-REFERENCE TO RELATED APPLICATION

This application claims the benefit of U.S. patent application Ser. No. 62/019,183, filed Jun. 30, 2014, the disclosure of which is hereby incorporated by reference in its entirety.

BACKGROUND

Lymphedema is a chronic, progressive, debilitating disease believed to affect nearly 10 million people in the US, most commonly as a sequela of breast or gynecological cancer treatment. While lymphedema rates depend on the type of procedure performed, they can be as high as 65% in the upper extremity following axillary lymph nodal radiation therapy, and up to 41% and 67% in the lower extremities after pelvic and inguinal-femoral lymph node dissections respectively.

While the majority of lymphedema patients can be adequately managed with conservative physiotherapy, advances in microsurgical techniques for lymphatico-venous anastomosis (LVA) have led to this procedure being increasingly performed. This in turn has prompted the development of safe, non-invasive techniques for pre-operative lymphatic mapping—requisite as small subdermal lymphatics and venules must be identified for performing the anastomosis. This role has historically been filled by radionuclide lymphoscintigraphy, which is limited by its low inherent spatial resolution and patient exposure to ionizing radiation.

Recently magnetic resonance (MR) lymphangiography (MRL) has emerged as a non-invasive alternative that allows for imaging an entire extremity with sufficient spatial and temporal resolution to aid in defining individual lymphatic channels prior to LVA surgery. MRL is somewhat analogous to MR angiography, using 3D spoiled gradient echo imaging. For MRL, however, gadolinium (Gd) contrast is injected intracutaneously in the web spaces of the hands or feet and followed dynamically as it slowly fills lymphatic channels. While this technique is effective, one often-confounding problem is concomitant venous enhancement, making it cumbersome to differentiate veins from lymphatics or generate an easily interpretable pure lymphatic map. In one recent study of 16 patients, 15 exhibited venous enhancement, with one so severe that evaluation of lymphatics was not possible (this case believed to be secondary to improper injection technique).

Our own clinical MRL experience mirrors this, with frequent confounding venous enhancement. Although it is usually possible to differentiate veins from lymphatics (particularly if i.v. Gd is administered at the end of the exam to enhance veins per the technique of Mitsumori et. al.), this a.) takes considerable time, and b.) makes it difficult to create an easy-to-interpret lymphatic-only map to clearly guide the surgeon. Instead, veins must be read around or meticulously labeled.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a product for use in MRI is provided. In one embodiment, the product comprises (1) a magnetic resonance imaging (MRI) contrast agent that contains gadolinium(III) and (2) an MRI suppression agent that is a blood pool agent for use in an MRI imaging method;
wherein the MRI suppression agent has a first $r2^*$;
wherein the MRI contrast agent has a second $r2^*$; and
wherein the first $r2^*$ is greater than the second $r2^*$.

In another aspect, a kit for use with magnetic resonance imaging (MRI) is provided. In one embodiment, the kit includes:
an MRI contrast agent that contains gadolinium(III); and
an MRI suppression agent that is a blood pool agent;
wherein the MRI suppression agent has a first $r2^*$;
wherein the MRI contrast agent has a second $r2^*$; and
wherein the first $r2^*$ is greater than the second $r2^*$.

In another aspect, a composition is provided that includes:
an MRI contrast agent that contains gadolinium(III) and is a non-blood pool agent; and
an MRI suppression agent that is a blood pool agent;
wherein the MRI suppression agent has a first $r2^*$;
wherein the MRI contrast agent has a second $r2^*$; and
wherein the first $r2^*$ is greater than the second $r2^*$.

In another aspect, an imaging system is provided, comprising:
a magnetic resonance imaging (MRI) system;
an MRI contrast agent according to any of the disclosed embodiments; and
an MRI suppression agent according to any of the disclosed embodiments.

In another aspect a method of producing a magnetic resonance imaging (MRI) image is provided. In one embodiment, the method includes MRI imaging a subject in a first location affected by both an MRI contrast agent and an MRI suppression agent.

In another aspect, a method of producing a magnetic resonance imaging (MRI) image is provided. In one embodiment, the method includes MRI imaging in a location wherein an MRI suppression agent according to the disclosed embodiments is uniquely resident by utilizing $T2^*$ weighting at which signal related to the MRI suppression agent is suppressed while signal is present due to an MRI contrast agent according to the disclosed embodiments.

Accordingly, in another aspect, a method of producing a magnetic resonance imaging (MRI) image is provided. In one embodiment, the method includes the steps of:
administering an MRI contrast agent according to the disclosed embodiments to a subject;
administering an MRI suppression agent according to the disclosed embodiments to the subject; and
MRI imaging the subject in a location affected by both the MRI contrast agent and the MRI suppression agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

Blood and plasma plotted on the same axes to demonstrate the much greater R2* elongation in blood with increasing ferumoxytol concentration.

Figure 2:
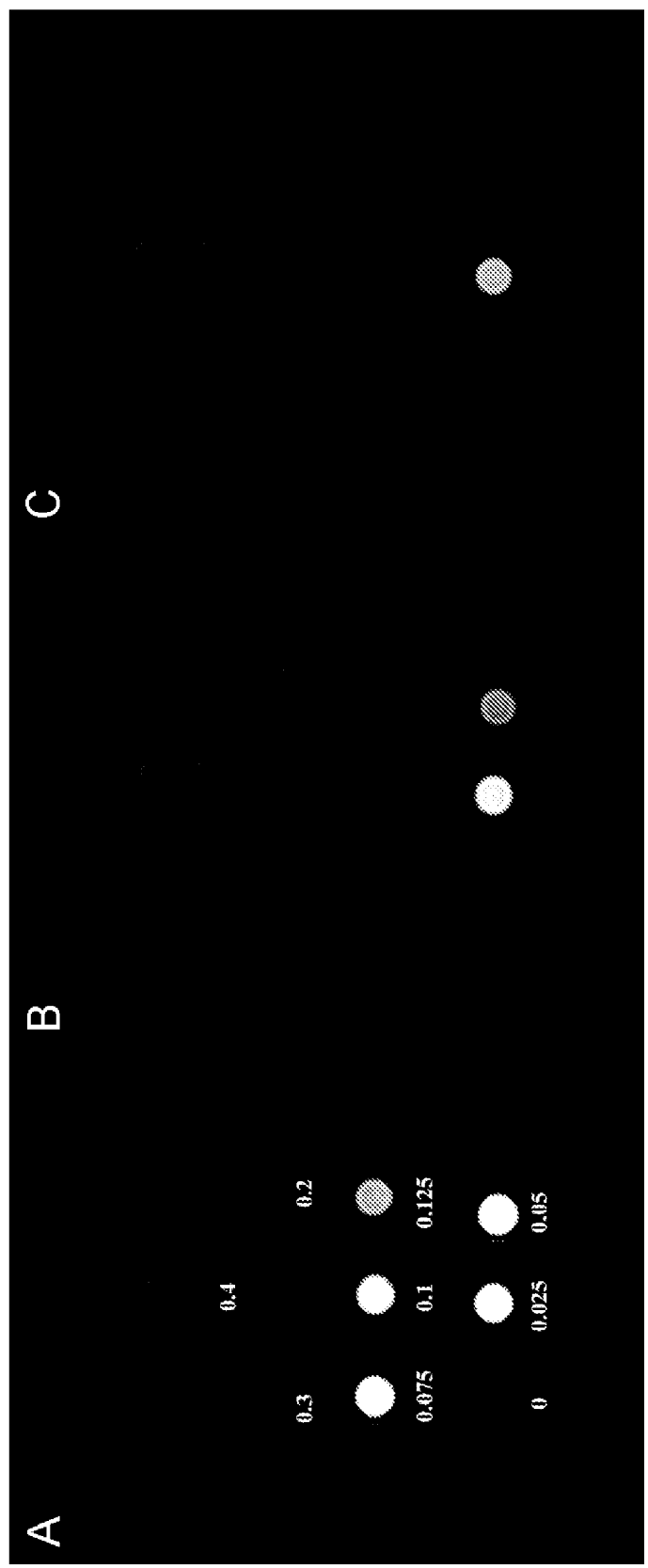

FIG. 2: 3 T mDixon water-reconstructed images from blood phantom doped with ferumoxytol; concentrations ranging from 0-0.4 mg/mL (concentrations (mg/mL) labeled in (a)). mDixon (a) TE pair=1.3/2.3 ms, (b) TE pair=3.6/4.6 ms, (c) TE pair=5.9/6.9 ms. Note near suppression of 0.075 mg/mL and complete suppression of 0.1 mg/mL (approximate anticipated blood concentration range at a dose of 5 mg/kg) for the TE=3.6/4.6 ms image (b), and complete suppression of both at TE=5.9/6.9 ms (c).

Figure 3:
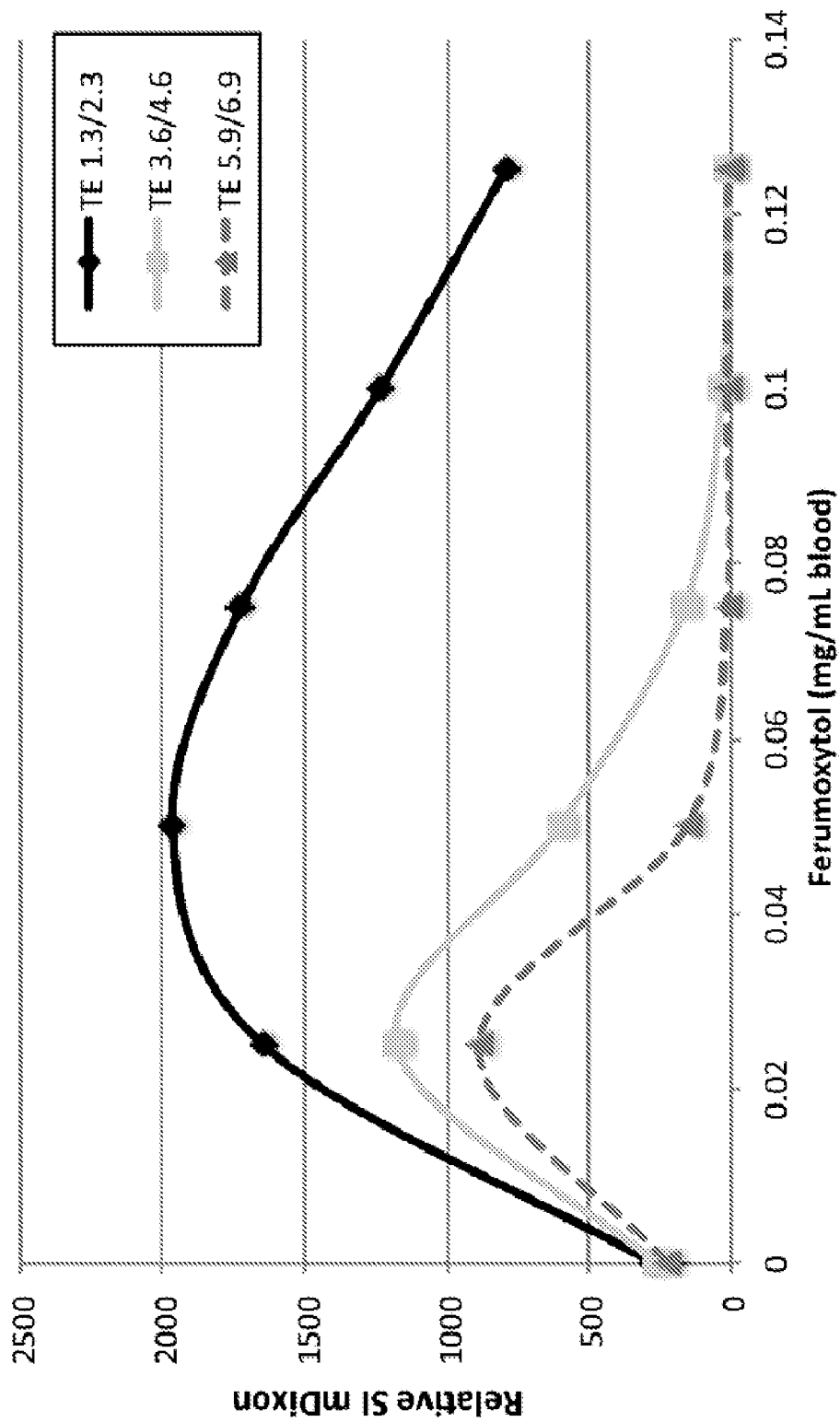

FIG. 3: mDixon signal intensity in blood phantoms (FIG. 2) plotted vs. blood ferumoxytol concentration for three different echo time combinations as shown. Note the shortest echo time combination allows for good vascular contrast (i.e. angiography) over this concentration range, while the longer echo time combinations effectively suppress vascular SI at higher ferumoxytol concentrations.

Figure 4:
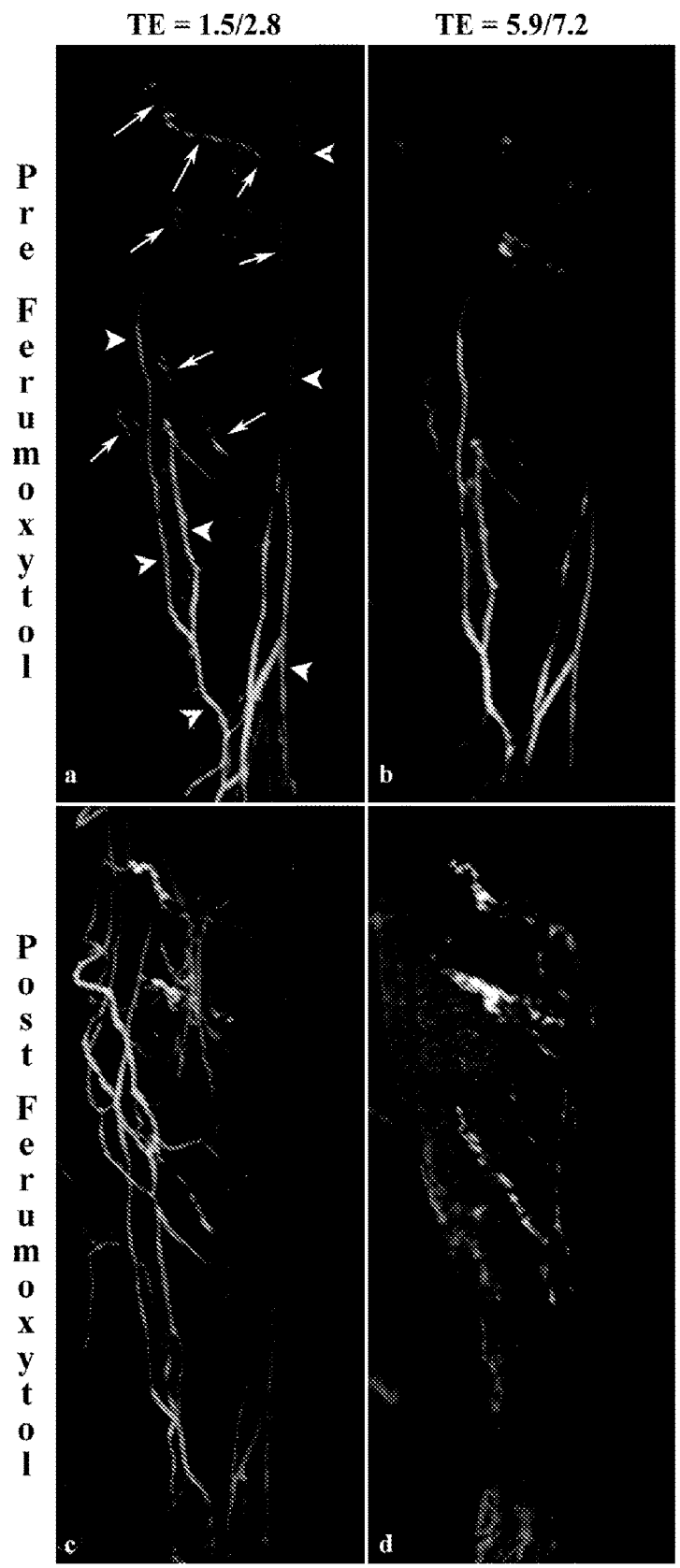

FIG. 4: Upper extremity (forearm) MRL MIP's approximately 30-40 minutes post intracutaneous gadolinium administration. (a) Demonstrating lymphatics (arrows) with confounding venous enhancement (arrowheads) using standard short echo contrast-enhanced MRL technique. (b) Immediately following lengthened TE combination to 5.9/7.2 ms—both veins and lymphatics remain enhanced. (c) Standard MRL after ferumoxytol 5 mg/kg. T1 shortening with short echo provides excellent vascular map—lymphatics can still be seen. (d) DARC-MRL post ferumoxytol demonstrates complete vascular suppression with persistent lymphatic enhancement and excellent "road-map" view. Many additional lymphatics can now be appreciated, particularly in the distal forearm. Note that there is clear SNR loss due to the lengthened TE (b, d), although lymphatic to background contrast remains high.

Figure 5:

FIG. 5: (a-c) Lower extremity low resolution mDixon MIP images approximately 3-5 min after injection of ferumoxytol 5 mg/kg (but pre-intracutaneous Gd). Three increasing echo time combinations performed (a-c) to determine where complete vascular suppression obtained. For this patient, TE=5.8/6.8 ms was used, with (d) demonstrating DARC-MRL MIP approximately 30 min after injection of intracutaneous gadolinium. Multiple lymphatics appreciated (arrows) with no venous enhancement.

Figure 6:
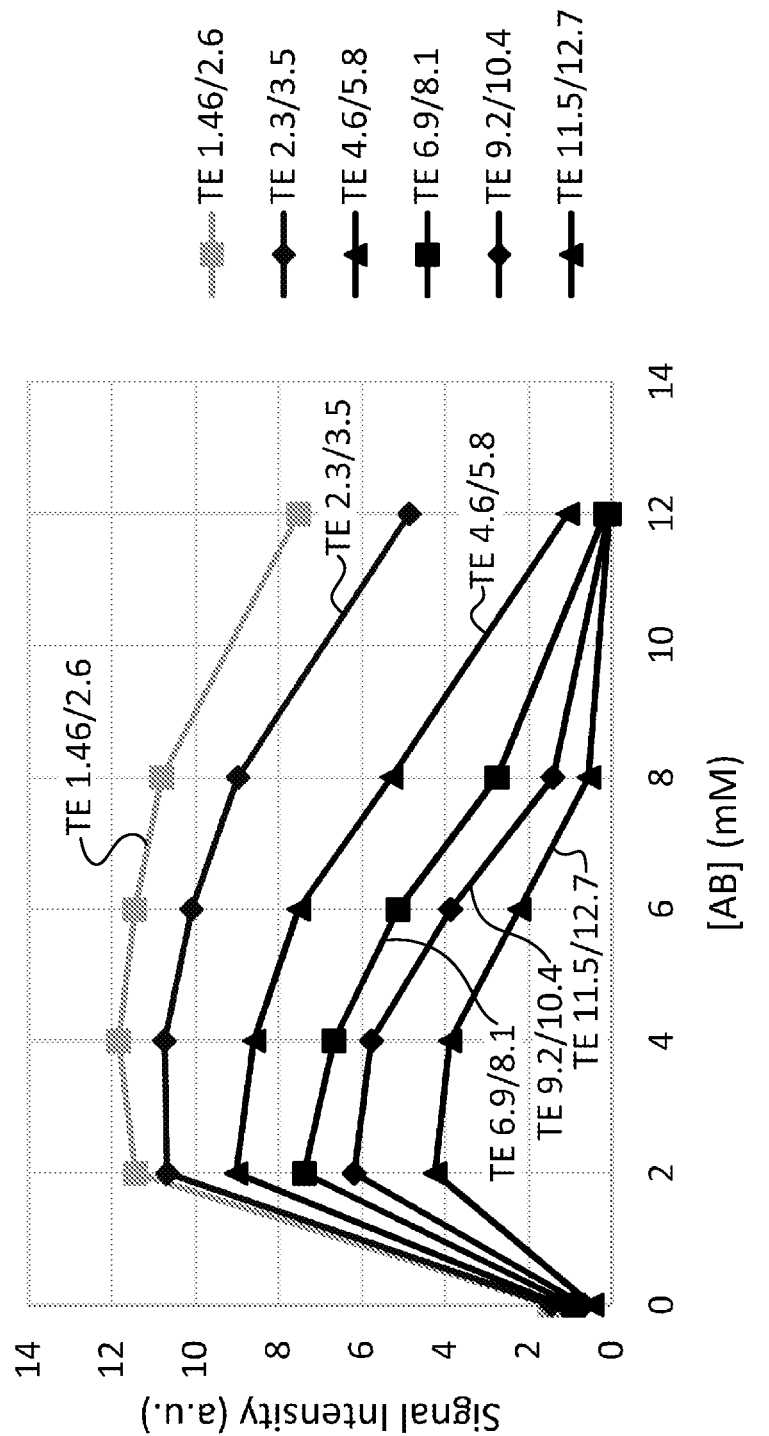

FIG. 6: Graphical summary of MRI data obtained using Ablavar, a Gd-containing blood-pool agent in blood. Relative signal intensity with mDixon imaging at specified echo times shown vs. Ablavar blood concentration.

Figure 7A:
Figure 7B:
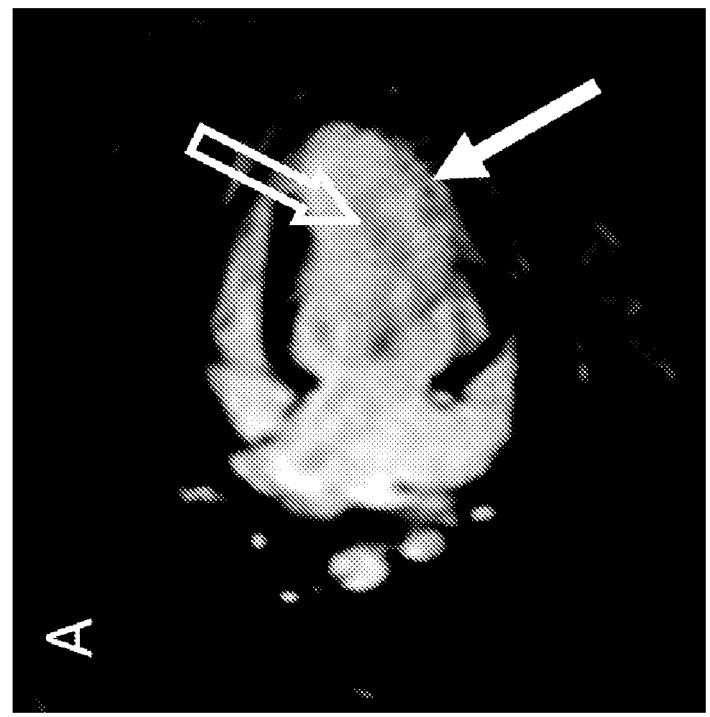

FIG. 7: Gadolinium enhanced imaging of a myocardial scar. Often myocardial scar, particularly if subendocardial (FIG. 7a, solid arrow) is difficult to differentiate from the left ventricular blood (7a, hollow arrow). In this case, both scar and blood contain Gd contrast agent and appear bright. With the addition of ferumoxytol (FIG. 7b), the blood pool (FIG. 7b, hollow arrow) signal intensity is suppressed compared to background tissue, and the contrast between blood pool and myocardial scar is heightened.

DETAILED DESCRIPTION

To solve the problem of differentiating veins from lymphatics in MRI images, among other uses, the disclosed embodiments relate to compositions, kits, systems, and methods that include an MRI contrast agent and an MRI suppression agent that is also a blood pool agent. Using appropriate MRI techniques, the MRI suppression agent will suppress signal in its location, while signal from the MRI contrast agent in other locations will not be suppressed. The result is a clarified MRI image with only non-vascular regions enhanced.

Definitions

Magnetic resonance imaging (MRI) System: Applies a magnetic field to create net magnetization from the subject's protons. Radio-frequency (RF) fields excite the protons to create detectable signal. RF coils detect the signal. Spatial location is encoded by magnetic field gradients. Image reconstruction typically includes Fourier transform of the acquired data. A "spin echo" can be created by application of an RF pulse to partially refocus transverse magnetization. A "gradient echo" can be created by proper application of gradient pulses to partially refocus transverse magnetization.

T1: longitudinal relaxation time constant.

T2: transverse relaxation time constant when signal is measured during a spin echo.

T2*: transverse relaxation time constant when signal is measured during a gradient echo.

R1: longitudinal relaxation rate constant (=1/T1).

R2: transverse relaxation rate constant when signal is measured during a spin echo (=1/T2).

R2*: transverse relaxation rate constant when signal is measured during a gradient echo (=1/T2*).

r1: contrast agent longitudinal relaxivity; the slope of R1 vs. contrast concentration.

r2: contrast agent transverse relaxivity when signal is measured during a spin echo; defined as the slope of R2 vs. contrast concentration.

r2*: contrast agent transverse relaxivity when signal is measured during a gradient echo; defined as the slope of R2* vs. contrast concentration.

r2* "in blood" refers to the relaxivity of a particular contrast (or suppression) agent in whole blood. It relates blood R2* to the concentration of contrast agent in the blood, and is typically much greater than r2* in plasma, saline, or other non-cellular medium. Most often, the relationship is approximated as a linear relationship between contrast agent concentration ([CA]) and R2* such that $R2^*=[CA] \times r2^*+k$, where k is blood R2* in the absence of contrast agent. Because of potential deviations from linearity in the relationship, r2* measurements must be performed over the range of useful concentrations.

As used herein, the term "blood pool agent" generally defines an agent having an intravascular half-life of 20 minutes or greater. Agents in blood will be removed from blood through leakage, degradation, and/or removal by the body. As an example, the half-life of Feraheme is about 10-15 hours, making it an excellent blood-pool agent. Ablavar has a half-life of about 30 minutes, making it a blood-pool agent by this basic definition, although not as good as Feraheme. According to certain embodiments, the MRI suppression agent is a superior blood pool agent, having an intravascular half-life of 1 hour or greater.

As used herein, the term "bodily compartment" indicates a unique space in the body where administered contrast agents can accumulate, such as blood vessels (arteries, veins, arterioles, venules, capillaries etc.), lymphatics, joint capsules, hollow viscus such as bowel or gallbladder, extracellular fluid compartment, region of fibrous scarring etc.

As used herein, the term "about" indicates that the subject number can be modified by plus or minus 10% and still fall within the described embodiment.

MRI Imaging Product

In one aspect, a product for use in MRI is provided. In one embodiment, the product comprises (1) a magnetic resonance imaging (MRI) contrast agent that contains gadolinium(III) and (2) an MRI suppression agent that is a blood pool agent for use in an MRI imaging method;

wherein the MRI suppression agent has a first r2*;
wherein the MRI contrast agent has a second r2*; and
wherein the first r2* is greater than the second r2*.

When disposed within a location (otherwise referred to as a region of interest (ROI)) within a subject, the product or combination of the MRI suppression agent and the MRI contrast agent can be used cooperatively, under certain MR conditions, to clarify imaging of the location by suppressing signal in blood-containing regions of the location. Specifically, the MRI contrast agent will enhance the MR signal when not in the immediate presence of the MRI suppression agent. When the MRI contrast agent and the MRI suppression agent are co-located, no MR signal is present under specific conditions (e.g., relatively long echo time (TE)). Because the MRI suppression agent is a blood pool agent, any region containing blood will be suppressed or darkened, while non-blood regions that contain the MRI contrast agent will produce a signal and be imageable by MRI.

As used herein, the term "suppress" or "suppression" defines the MRI suppression agent's ability to "darken" or "turn off" MRI signal that would otherwise be generated at a location if not for the MRI suppression agent being present. Furthermore, suppression is not equal to a negative contrast agent. Instead, the MRI suppression agent actually eliminates signal from obscuring structures, due to its r2* characteristics and the MRI parameters used, as will be described in further detail below.

One exemplary benefit of the disclosed MRI suppression agent is the ability to "darken" or "turn off" vasculature MRI signal in order to eliminate it from MR lymphangiography (MRL) images, for example, which provides the benefit of allowing lymphatics to be clearly imaged without the traditional difficulty of having to distinguish between veins and lymphatics. Example 1 herein provides an expanded treatment of the disclosed compositions and methods applied to MRL to great benefit.

Table 1 presents r2* calculations for representative MRI contrast agents and MRI suppression agents useful in the disclosed embodiments. Feraheme and Ablavar are representative MRI suppression agents (Examples 1 and 2 describe experimental results related to Feraheme and Ablavar, respectively). Ablavar can also be an MRI contrast agent (if used with Feraheme or another higher-r2* agent). The other listed agents are MRI contrast agents.

TABLE 1

Approximate r2* relaxivity (mM$^{-1}$ sec$^{-1}$) determined experimentally[1]

| | r2* plasma 1.5 T | r2* plasma 3 T | r2* blood 1.5 T | r2* blood 3 T |
|---|---|---|---|---|
| Feraheme | 120 | 120 | 580 | 580 |
| Ablavar | 12 | 14 | 22 | 34 |
| MultiHance | 7 | 11 | 17 | 32 |
| Gadavist | 5 | 11 | 17 | 32 |
| ProHance | 5 | 10 | 15 | 29 |
| "Typical" Gd agent[2] | 5-7 | 10-12 | 15-17 | 29-32 |

[1]r2*determined using methods disclosed in Examples.
[2]"Typical" Gd agents not specifically listed in Table 1 include Dotarem, Eovist, Magnevist, Omniscan, and OptiMark.

Contrast Agent

The MRI contrast agent (also referred to herein as the "contrast agent") can be any MRI contrast agent known to those of skill in the art. The contrast agent is Gd(III) containing and can be administered to a subject to enhance MRI. Generally, the contrast agent is selected for having as high an r1 as possible, so as to produce as much MR signal as possible when T1 weighted imaging is performed. The contrast agent has an r2* that is lower than the r2* of the suppression agent. This mismatch in r2* between contrast agent and suppression agent leads to the suppression of MR signal that would have been generated by the contrast agent. As described herein, this suppression is alternately referred to as "darkening" or "turning off" the MR signal. In order to adequately suppress the contrast agent, the two agents must be co-located (e.g., within the same bodily "compartment" containing blood). The two agents are mixed together in the blood and signal suppression results if sufficient suppression agent is present to suppress the contrast agent for the type of imaging being performed. The amount of suppression agent required varies based on the suppression agent, the contrast agent, and the compartment of desired signal suppression. Experimental determination of the amounts of each agent can be determined by using the appropriate techniques, as disclosed herein, including relatively lengthened TE, which will darken the blood signal due to the suppression agent, if the suppression agent is present in sufficient amount and mixed in the blood with the contrast agent.

In certain embodiments, the r2* of the MRI contrast agent is from 10 to 55 s$^{-1}$/mM in blood.

In one embodiment, the MRI contrast agent is selected from the group consisting of Gadopentate dimeglumine (Magnevist), Gadobutrol (Gadavist, Gadovist), Gadoteridol (ProHance), Gadobenate dimeglumine (MultiHance), Gadodiamide (Omniscan), Gadoversetamide (OptiMARK), Gadoteric acid (Dotarem), Gadoxetate disodium (Eovist, Primovist), and Gadofesveset trisodium (Ablavar).

In one embodiment, the MRI contrast agent is an injectable contrast solution. In one embodiment, the injectable solution is an aqueous solution. Solution-based injection is the typical method for delivering the MRI contrast agent to ROI of the subject. In certain embodiments, such as for MRL, the MRI contrast agent is injected into a different bodily "compartment" than the MRI suppression agent. For MRL, the MRI contrast agent is injected intracutaneously, so as to affect lymphatics. Conversely, the MRI suppression agent is injected intravenously so as to suppress MR signal in affected veins.

In a further embodiment, the injectable contrast solution comprises the MRI contrast agent at a concentration of about 0.1 M to about 1.0 M. In terms of commercially available MRI suppression agents, Gadavist is the highest packaged concentration Gd-based contrast agent at 1 M. Most Gd-based contrast agents are 0.5 M and Ablavar is 0.25 M.

In one embodiment, the MRI contrast agent is not a blood pool agent. In such embodiments, the contrast agent is meant to extend beyond blood-containing compartments of the subject, such as into lymphatics during an MRL procedure. Almost all Gd-containing agents are non-blood pool agents. Ablavar is a notable exception.

Suppression Agent

The MRI suppression agent (also referred to herein as the "suppression agent") is a blood pool agent with an r2* in blood greater than the r2* of the co-located MRI contrast agent. Co-location refers to the two agents being disposed in blood in the same bodily compartment to be imaged. By remaining in blood and having a greater r2* than the contrast agent, under certain MRI conditions the suppression agent will suppress blood MR signal, thereby allowing blood-containing areas to be dark or "turned off" in the resulting MR image.

In certain embodiments, the r2* of the MRI suppression agent is from 10 to 600 $s^{-1}$/mM.

In one embodiment, the MRI suppression agent is selected from the group consisting of an ultrasmall superparamagnetic iron oxide (USPIO) and a gadolinium-containing blood pool agent.

In one embodiment, the MRI suppression agent is the gadolinium-containing blood pool agent gadofosveset trisodium (Ablavar).

In one embodiment, the MRI suppression agent is the USPIO ferumoxytol (Feraheme).

In one embodiment, the MRI suppression agent is an injectable suppression solution. In one embodiment, the injectable solution is an aqueous solution. In a further embodiment, the injectable suppression solution comprises the MRI suppression agent at a concentration of about 0.05 to about 1.0 M. In terms of commercially available MRI suppression agents, Feraheme is packaged as 510 mg Fe/17 ml/(55.845 g/mol)=0.54 M Fe and Ablavar is 0.25 M. The maximum commercial suppression agent concentration is about 1 M. Dilution down to about 0.05 M of commercial suppression agents can be useful in order to control the amount of suppression agent administered.

In one embodiment, the MRI contrast agent is Ablavar and the MRI suppression agent is Feraheme. While Ablavar can be used as an MRI suppression agent when properly paired with an agent having a lower r2*, when Ablavar is paired with Feraheme, which possesses a very large r2*, the Ablavar acts as the MRI contrast agent and the Feraheme acts as the MRI suppression agent. This combination is of interest because Ablavar has a very high r1 compared to other contrast agents, particularly when bound to protein, and may be the best agent for indications such as MR lymphangiography or instances where attempting to visualize Ablavar "leaking" out of the blood pool into tissues.

In one embodiment, the MRI contrast agent is MultiHance and the MRI suppression agent is Feraheme. MultiHance is a well-known (non-blood pool) contrast agent with somewhat increased r1 and a large r2* difference when compared to Feraheme that results in a pairing that produces desirable results using agents that clinicians are comfortable working with.

MRI Imaging Kit

In one aspect, a kit for use with magnetic resonance imaging (MRI) is provided. In one embodiment, the kit includes:
  an MRI contrast agent that contains gadolinium(III); and
  an MRI suppression agent that is a blood pool agent;
  wherein the MRI suppression agent has a first r2*;
  wherein the MRI contrast agent has a second r2*; and
  wherein the first r2* is greater than the second r2*.

The MRI contrast agent and MRI suppression agent of the kit can be any of those described elsewhere herein. The kit provides the MRI contrast agent and the MRI suppression agent in a convenient package, although the two agents are not in the same solution, but instead are in two different solutions that define the kit. As an example, in one embodiment the kit comprises Feraheme as the MRI suppression agent and Ablavar as the MRI contrast agent. In another embodiment, the kit comprises Feraheme as the MRI suppression agent and MultiHance as the MRI contrast agent. In other embodiments, the kit consists essentially of the MRI suppression agent (e.g., Feraheme) and the MRI contrast agent (e.g., MultiHance). In one embodiment, both solutions are aqueous solutions.

Combined Composition

In another aspect, a composition is provided that includes:
  an MRI contrast agent that contains gadolinium(III) and is a non-blood pool agent; and
  an MRI suppression agent that is a blood pool agent;
  wherein the MRI suppression agent has a first r2*;
  wherein the MRI contrast agent has a second r2*; and
  wherein the first r2* is greater than the second r2*.

Similar to other aspects, the composition includes both an MRI contrast agent and an MRI suppression agent, as disclosed herein. Unlike the kit aspects and embodiments, the composition is a single composition that includes both the MRI contrast agent and the MRI suppression agent. Such a composition is useful for applications where it is desirous for the two agents to be administered into the same bodily compartment. This is unlike in MRL where the two agents are administered separately to separate bodily compartments. Representative techniques for which the single composition approach is useful include imaging tumors using dynamic contrast, as will be described in further detail below.

In one aspect, the MRI contrast agent and the MRI suppression agent are together in an injectable solution. An injectable solution is the typical administration route. In one embodiment, the injectable solution is an aqueous solution.

MRI Systems

In another aspect, an imaging system is provided, comprising:
  a magnetic resonance imaging (MRI) system;
  an MRI contrast agent according to any of the disclosed embodiments; and
  an MRI suppression agent according to any of the disclosed embodiments. In this aspect, the MRI contrast agent and the MRI suppression agent can be any of those disclosed herein. Additionally, this aspect includes an MRI system capable of generating an MRI image demonstrating the signal suppression provided by the MRI suppression agent. Such MRI systems are generally known and include any MRI system that is capable of performing a T1-weighted sequence with the ability to achieve concomitant T2* weighting with magnitude or phase-based reconstruction.

Representative compatible MRI systems include those sold by Philips (Best, the Netherlands), such as the 1.5 T Achieva and 3 T Ingenia.

In one embodiment, the MRI system is capable of performing a 2 or 3 point Dixon sequence, such as mDixon, which is a proprietary Philips sequence that allows for the necessary T1-weighted sequence with the ability to achieve concomitant T2* weighting.

In one embodiment, the MRI system is capable of performing a phase-based reconstruction, such as susceptibility weighted imaging.

MRI Methods

Turning now to methods of using the MRI suppression agent and the MRI contrast agent, in another aspect a method of producing a magnetic resonance imaging (MRI) image is provided.

In one embodiment, the method includes MRI imaging a subject in a first location affected by both an MRI contrast agent and an MRI suppression agent. The subject is imaged in the first location using any compatible MRI system. But for the MRI suppression agent, the generated MRI image would image (detect signal enhancement from) the MRI contrast agent in the first location. However, because of the MRI suppression agent, no signal (or negligible signal) is generated and the first location appears dark. In MRL, the first location is vasculature. Therefore, in a related embodiment, a method of MRL is provided wherein the MRI suppression agent darkens vasculature in which the MRI suppression agent and MRI contrast agent are disposed.

In one embodiment, a first R2* in the first location is greater than a second R2* in a second location that includes MRI contrast agent but not MRI suppression agent. When imaging a region of interest that includes at least two locations (e.g., vasculature and lymphatics in a common area, such as an arm or leg), the goal of the method is to darken the blood in the MRI image and allow the non-blood location to be imaged regularly. This is accomplished in the present embodiment by introducing agents that allow for the imbalance between R2* in the different locations. The greater R2* achieved by the agent produces darkening when using appropriate MRI parameters (e.g., relatively long TE). Relatively large R2* is achieved in certain embodiments by using an MRI suppression agent having a relatively large r2* compared to the MRI contrast agent used.

In other embodiments of the method, a first magnetic susceptibility in the first location is greater than a second magnetic susceptibility in a second location that includes MRI contrast agent but not MRI suppression agent. Similar to the above embodiments related to R2*, embodiments related to magnetic susceptibility rely on MRI-detectable differences between a location having only the contrast agent compared to a location having both the contrast agent and the suppression agent. In particular, by adding the suppression agent to blood containing the contrast agent, the magnetic susceptibility in the compartment is altered (raised), which creates a MR signal phase shift in the compartment that can be measured in the generated MRI images. In particular, phase shift between the two compartments can be used to image the different magnetic susceptibility. Therefore, these embodiments rely on a "phase-based" method to suppress signal, whereas the "T2*-weighted" methods described elsewhere herein used "magnitude" images rather than "phase" images.

One benefit of such a phase-based technique is that a single (relatively short) echo time can be used to produce images of the location both with "suppression" and without. In this regard, the location can be imaged without suppression using magnitude imaging; and the same scan can be reconstructed using phase imaging to darken the signal where the suppression agent is present. This method is in contrast to the T2*-related methods (e.g., TE lengthening) that require multiple echo times to be used to produce images of the location with and without darkening due to suppression. This method may be referred to as "phase-based" imaging or "susceptibility-weighted" imaging.

The blood r2* of a contrast agent is directly related to the magnetic "susceptibility" of the contrast agent.

R2* can be measured for a contrast or suppression agent by performing a multi-echo gradient echo pulse sequence (e.g. short echo spacing 1-2 ms, >24 echoes) of the solution at the concentration of interest, and then measuring signal intensity (SI) from a region of interest for each echo of the resultant images. SI from each echo is then plotted vs. TE and fit to an exponential decay curve (e.g. $M_0 e^{-(TE*R2*)}$) to determine R2*.

To determine r2* for the agent of interest, R2* measurements as above must be performed at varying concentrations of the agent. R2* can then be plotted vs. agent concentration. The r2* is generally considered to be the "slope" of a fitted line. However, r2* vs. concentration is not necessarily linear, depending on concentration range, field strength and solvent (or bodily fluid) in which the contrast agent is contained. In such cases r2* is typically estimated over specific concentration ranges. Accurate blood r2* must be measured under physiologic conditions (e.g., physiologic oxygenation, pH, temperature, hematocrit) in whole blood over the contrast agent concentration range of interest.

In one embodiment, the first location and the second location are in different bodily compartments. In one embodiment, the first location is a venous location and the second location is a lymphatic location.

In one embodiment, MRI imaging the subject comprises the steps of:

generating a first MRI image with a first T2*-weighting, whereby a signal related to the MRI suppression agent is not suppressed; and generating a second MRI image with second T2*-weighting, greater than the first T2*-weighting, such that the signal related to the MRI suppression agent is suppressed.

As used herein, the term "signal related to" means signal that would be generated in the presence of the agent.

In one embodiment, generating the first MRI image is performed at a first echo time (TE); and wherein generating the second MRI image is performed at a second TE that is longer than the first TE.

In one embodiment, the first TE is from 0.1 ms to 3 ms.

In one embodiment, the second TE is from 3 ms to 30 ms.

In one embodiment, MRI imaging comprises applying a magnetic field of about 0.5 T to about 7.0 T.

In one embodiment, the method is a lymphangiography method, such as MRL.

In one embodiment, the method is used to image vessel wall or cardiac tissue. Example 3 presents experimental results illustrating suppression of blood signal in cardiac tissue in order to image a scarred area.

In one embodiment, the method is used to image tissue, organ, or a tumor by dynamic contrast enhancement.

In yet another aspect, a method of producing a magnetic resonance imaging (MRI) image is provided. In one embodiment, the method includes MRI imaging in a location wherein an MRI suppression agent according to the disclosed embodiments is uniquely resident by utilizing T2* weighting at which signal related to the MRI suppression agent is suppressed while signal is present due to an MRI contrast agent according to the disclosed embodiments.

In one embodiment, the T2* weighting is produced at an echo time (TE) at which signal related to the MRI suppression agent is suppressed while signal is present due to the MRI contrast agent.

In one embodiment, the MRI images are reconstructed with phase-based reconstruction, suppressing the signal related to the MRI suppression agent while signal is present due to the MRI contrast agent.

A method of producing a magnetic resonance imaging (MRI) image, comprising:

MRI imaging a subject in a location affected by both an MRI contrast agent according to the disclosed embodiments and an MRI suppression agent according to the disclosed embodiments;

wherein the MRI contrast agent and the MRI suppression agent are both pre-delivered to the location.

Any of the methods elsewhere described herein can be modified to include a step of administering at least one, or both of, the MRI contrast agent and the MRI suppression agent. In the following method, the steps of administration are made explicit. Accordingly, in another aspect, a method of producing a magnetic resonance imaging (MRI) image is provided. In one embodiment, the method includes the steps of:

administering an MRI contrast agent according to the disclosed embodiments to a subject;

administering an MRI suppression agent according to the disclosed embodiments to the subject; and MRI imaging the subject in a location affected by both the MRI contrast agent and the MRI suppression agent.

While similar to previously described methods, the method of this aspect is distinct by additionally including steps of administering the MRI contrast agent and the MRI suppression agent to the subject. The administering steps comprise injection into the appropriate bodily compartment to provide the desired effect.

In one embodiment, the step of administering the MRI contrast agent is performed before the step of administering the MRI suppression agent. The length of time between administrations is on the order of minutes, typically, so as to allow both agents to be present in effective concentrations. Because the MRI contrast agent, in certain embodiments, is a non-blood pool agent, administration prior to the MRI suppression agent will allow greater time for the contrast agent to diffuse throughout the region of interest.

In one embodiment, the step of administering the MRI suppression agent is performed before the step of administering the MRI contrast agent. The length of time between administrations is on the order of minutes, typically, so as to allow both agents to be present in effective concentrations. However, the length of time can be on the order of hours if the half-life is sufficient (e.g., Feraheme's 15 hour half-life). Administering the MRI contrast agent prior to the MRI suppression agent may be beneficial if it is desired to image the vasculature prior to lymphatics in an MRL method. Once the vasculature is imaged, the MRI suppression agent can be administered and the vasculature signal darkened such that only lymphatics are imaged.

In one embodiment, the step of administering the MRI suppression agent is performed concurrently with the step of administering the MRI contrast agent. Concurrent administration can simplify a procedure by providing a common administration time. Concurrent administration is also inherent if the MRI contrast agent and the MRI suppression agent are combined in a common composition (e.g., solution).

The following examples are included for the purpose of illustrating, not limiting, the described embodiments.

EXAMPLES

Example 1

MR Lymphangiography Using Feraheme (USPIO) Suppression Agent

To solve the problem of differentiating veins from lymphatics in MRI images, this example presents a technique (Dual-Agent Relaxivity Contrast (DARC)) for suppressing potentially enhancing veins in magnetic resonance lymphangiography (MRL) using the FDA-approved ultrasmall superparamagnetic iron oxide (USPIO) ferumoxytol (Feraheme, AMAG Pharmaceuticals, Inc., Waltham, Mass. Venous suppression can be achieved based on the increased blood R2* due to intravascular (but not intralymphatic) ferumoxytol in combination with appropriately lengthened echo times (TE) for the MRL gradient echo sequence.

Objective: Develop and demonstrate a technique to eliminate venous enhancement in contrast-enhanced MR Lymphangiography through shortening T2* in the blood pool, thus allowing for a lymphatic-only map.

Conclusion: Administration of the blood pool iron agent ferumoxytol in addition to intracutaneous gadolinium during contrast-enhanced MR Lymphangiography allows for suppression of vascular structures to achieve venous-free lymphatic mapping.

Technique

Suppression Agent

Ferumoxytol is an ultra-small super paramagnetic iron oxide (USPIO) initially conceived for MR imaging, however ultimately gaining FDA approval as an agent for iron supplementation in patients with renal insufficiency. The FDA-approved dose for iron supplementation is 510 mg (17 mL) as a single i.v. dose, followed by a second 510 mg i.v. dose 3-8 days later. The ferumoxytol USPIO nanoparticle is coated with a semisynthetic carbohydrate, having an average colloidal particle size of 6.4 m and a molecular weight of 731 kDa. The agent has a r1 relaxivity of 38 mM$^{-1}$ sec$^{-1}$ and a r2 relaxivity of 83 mM$^{-1}$ sec$^{-1}$ (1.5 T, 0.5% by weight agar gel), and is considered a blood-pool agent, having an intravascular half-life in normal subjects of 9.3-14.5 hours.

Ex Vivo Blood Study

In order to determine whether ferumoxytol could be effective in suppressing blood based on R2* signal loss, it was first necessary to determine the R2* relaxivity of ferumoxytol in human blood. To accomplish this, whole human venous blood was placed into nine 6 mL high density polyethylene tubes that were vertically embedded in a phantom tray filled with 2% agar, and the blood-containing tubes were doped with ferumoxytol to concentrations of 0, 0.025, 0.05, 0.075, 0.1, 0.125, 0.2, 0.3, and 0.4 mg/mL. The samples were kept at approximately 37° C. and intermittently inverted to prevent settling. R2* was measured using an 8 channel head coil at both 1.5 T (Philips Achieva, Best, the Netherlands) and 3 T (Philips Ingenia) with a single-slice multi gradient echo (mFFE) sequence [TR/TE/$\Delta$TE/$\alpha$/number of echoes=200 ms/1.5 ms/2.4 ms/35°/32]. To yield the effective R2*, average signal intensities from an ROI placed within each tube were fitted with mono-exponential decay curves using nonlinear least squares (Matlab, Mathworks, Natick, Mass.). In addition, the phantoms were imaged with a modified 3D Dixon technique (mDixon, Philips) with variable echo time pairs (e.g. at 3 T, TE1/TE2=1.3/2.3 ms, 3.6/4.6 ms, and 5.9/6.9 ms). The imaging plane was chosen such that the phantom tubes were fully embedded in agar to reduce susceptibility effects. Average Dixon signal intensity of a region-of-interest (ROI) in each sample was measured and plotted versus concentration of ferumoxytol. The samples were then allowed to settle (4 hours) such that the red blood cells layered out, and the R2* was re-measured in the plasma fraction.

Plasma and Blood R2* Determination

Figure 1:
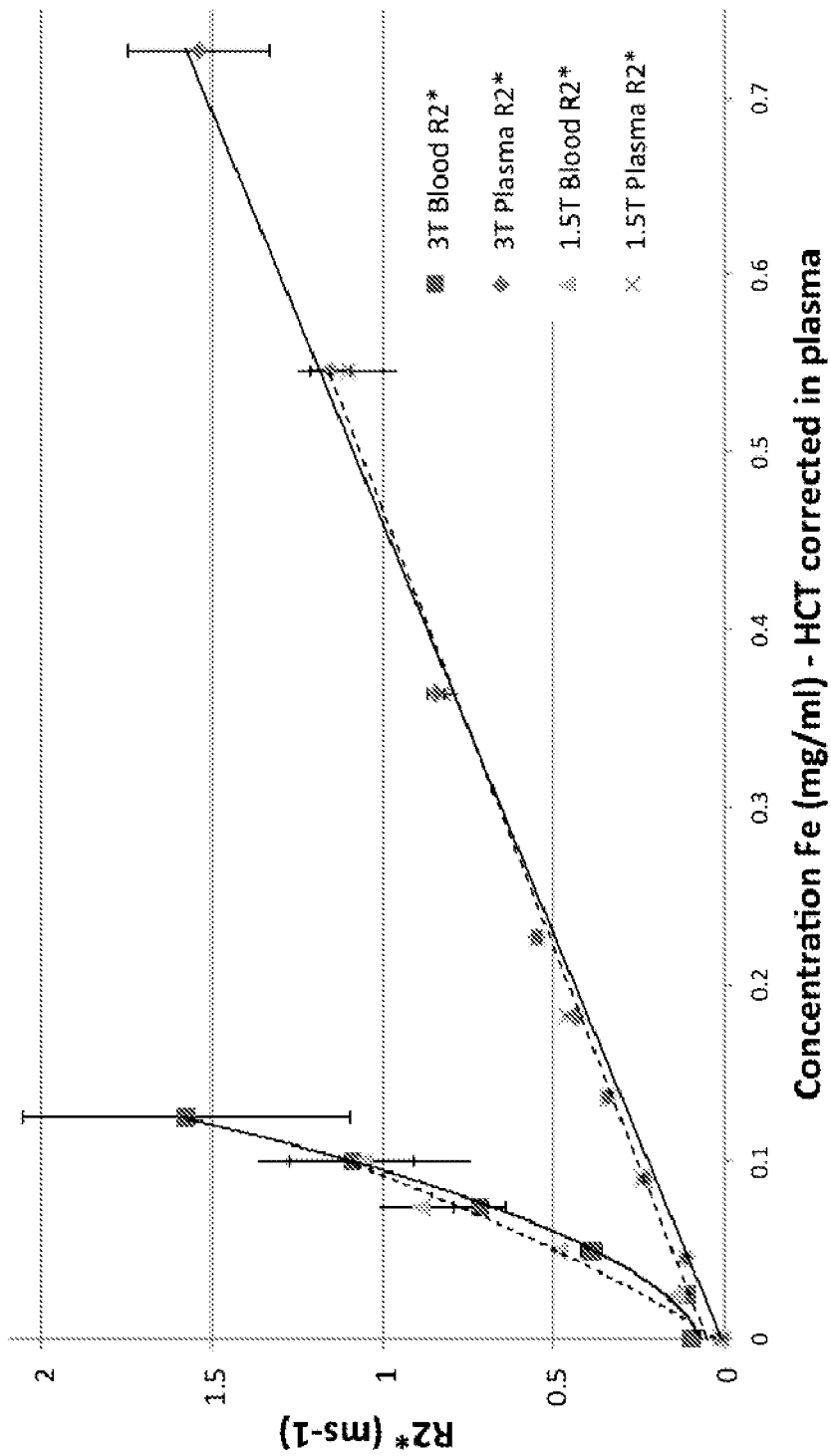
FIG. 1: $R2^*$ in plasma vs. plasma ferumoxytol concentration (mg/mL), and $R2^*$ in blood vs. blood ferumoxytol concentration (mg/mL); 1.5 T and 3 T. Curves represent linear fittings for plasma and quadratic fittings for blood, dashed curves are 1.5 T. Error bars represent error in $R2^*$ fit.

R2* values in plasma were linear with respect to concentration ($R^2 > 0.98$ at both field strengths) and independent of $B_0$ as shown in FIG. 1. R2* for the highest ferumoxytol concentration at 1.5 T could not be fit due to inadequate signal-to-noise ratio (SNR). Because of the linearity between ferumoxytol concentration and R2*, r2* "relaxivity" was defined reflecting the slope of the fit in FIG. 1 (i.e., r2*$_{plasma}$=slope of R2* vs. ferumoxytol concentration); r2*~2.1 mL mg$^{-1}$ ms$^{-1}$ (~120 mM$^{-1}$ sec$^{-1}$ in conventional relaxivity units) for both field strengths.

In venous blood, R2* was reasonably fit by quadratic dependence on ferumoxytol concentration ($R^2 > 0.97$ at both field strengths), and again was very similar for the two field strengths (FIG. 1). R2* increased with ferumoxytol concentration much more rapidly in blood than in plasma (FIG. 1).

R2* measurements were only possible up to 0.125 mg/mL at 3 T and 0.1 mg/mL at 1.5 T due to SNR limitations of our measurement technique.

In order to predict equilibrium blood concentrations of ferumoxytol, it was assumed the full dose was distributed throughout the intravascular space during the first hour post administration because of its blood-pool properties, with intravascular half-life approaching 15 hours. Given typical human intravascular volumes of 65, 75 mL/kg (female, male), a 5 mg/kg dose equates to a blood concentration approximating 0.077 mg/mL for women, and 0.067 mg/mL for men. Note that for both field strengths, an R2* of approximately 0.5 ms$^{-1}$ (i.e. T2*~2 ms) was achieved for ferumoxytol blood concentration~0.05 mg/mL (FIG. 1), which should be slightly exceeded by the 5 mg/kg dose.

Phantom Imaging

Representative mDixon phantom images are shown in FIG. 2. The signal intensity plotted from ROI's within these phantoms at different TE combinations are shown in FIG. 3. Using even the shortest feasible mDixon TE combination of 1.3/2.3 ms, the high r2* relaxivity of ferumoxytol in blood caused significant signal loss at a concentration of 0.2 mg/mL, and complete signal loss with severe susceptibility artifacts at yet higher concentrations (FIG. 2a). As TE increased, similar blood signal loss was seen at decreasing ferumoxytol concentrations (FIGS. 2b-c, 3), with complete suppression at concentrations ≥0.075 mg/mL for TE=5.9/6.9 ms, and substantial suppression at 0.05 mg/mL such that signal intensity (SI) was approximately equivalent to that of pure blood (FIG. 3). Note also that even for ferumoxytol concentrations up to and beyond 0.1 mg/mL there was relatively high SI for the shortest TE combination (1.3/2.3 ms), meaning good vascular enhancement was obtained using short-echo mDixon at the suggested ferumoxytol dose.

Clinical MR Lymphangiography

Our clinical standard MRL used a mixture of 5 mL gadobenate dimeglumine (MultiHance, Bracco Diagnostics, Princeton, N.J.) and 1 mL 1% lidocaine, of which 1 mL was injected intracutaneously into each webspace of the hand or foot of the extremity of interest (4 injections per imaged extremity). Subsequent multi-station dynamic MRL imaging was performed using a short-echo mDixon high-resolution 3D sequence covering the entire extremity including skin (representative Philips Ingenia 3T parameters, upper extremity: FOV 300×220×150 mm$^3$ with matrix 230×170× 94, true resolution 1.3×1.3×1.6 mm$^3$; lower extremity: FOV 320×435×180–225 mm$^3$ with matrix 212×290×90–112, true resolution 1.5×1.5×2.0 mm$^3$; TR/TE1/TE2/α=4.4 ms/1.5 ms/2.7 ms/20°, 1-1.5 min per station, 2 stations for upper extremity, 3 stations for lower extremity, water-only reconstruction) using a combination of the anterior torso phased array coil and built-in table phased array coil. Lymphatic imaging was typically carried out over an hour or more, with the endpoint and determination of which stations to image based on the technologist or radiologist's real-time assessment of lymphatic enhancement progression.

To add venous-suppressed (DARC) MRL, ferumoxytol 5 mg/kg (diluted with normal saline to a total volume of 60 mL) was administered in addition to intracutaneous gadolinium, and dual-agent 3D MRLs were obtained with increased mDixon echo time pairs (TE1, TE2) in order to null blood while preserving signal from the separate Gd-containing intralymphatic compartment. TE1 and TE2 were chosen such that the fat signal experienced an approximately 180° phase shift between the echoes for the field strength used, with each echo approximately in- or out-of-phase, and the longest echo time TE2 up to approximately 7.0 ms. The optimal combination of TE's for venous suppression was determined beginning 2 min after ferumoxytol injection by obtaining multiple rapid lower resolution (1.8×1.8×3.0 mm$^3$) 3D datasets at progressively lengthened TE combinations until complete venous suppression was noted on a MIP image. Once this combination of TE was determined, MRL proceeded using this mDixon TE pair. Description of the DARC-MRL technique, including proof-of-concept images from 2 patients, was reviewed by our local IRB office and determined not to require IRB approval for publication.

Clinical Example DARC MRL

Ferumoxytol was administered and mDixon MRL performed using lengthened TE combinations either after the intracutaneous injection of gadolinium to suppress enhancing veins, or pre-emptively prior to intracutaneous injection such that veins were suppressed from initiation of lymphatic enhancement. An example of the former is outlined in FIG. 4, where ferumoxytol was administered well after Gd administration, resulting in either a combined MRL/blood-pool angiogram (FIG. 4c) or a lymphatic only DARC-MRL (FIG. 4d). Note that while there was clear loss of SNR using lengthened TE, the complete suppression of vascular signal and high relative signal of gadolinium-containing lymphatics made for high contrast-to-noise (CNR) (FIG. 4d). FIG. 5 demonstrates the latter approach where ferumoxytol was administered prior to intracutaneous gadolinium such that vasculature was always suppressed (FIG. 5d) at lengthened TE. FIGS. 5a-5c also demonstrate the method by which the proper TE pair was chosen: examining increasing TE pairs until the vasculature was adequately suppressed.

Discussion

In order to more effectively and simply visualize lymphatic channels for lymphedema treatment planning, a clinical MR imaging technique (DARC) was developed that depicts only lymphatic channels while suppressing signal from any simultaneously enhancing veins.

As in previous MRL methods, a Gd-based contrast agent was intracutaneously injected such that it was taken up by lymphatics, and in many cases also by veins. In the new method, an additional contrast agent (USPIO) was injected intravenously where it remains exclusively intravascular, not entering the lymphatic channels. USPIO in the blood pool shortens the T2* in arteries and veins, allowing T2* mediated suppression of all vascular signal (lengthened TE) such that only Gd-containing lymphatics are visualized. By choosing a short TE, however, both lymphatics (if enhanced by gadolinium) and blood vessels can be visualized. Thus the DARC technique utilizes either short or long TE-pair Dixon imaging to selectively "turn-on" or "turn-off" venous signal, facilitating identification and localization of lymphatic channels. While not all MRL cases demonstrate severe venous enhancement, many do, particularly if the injection is not entirely intracutaneous, which can be difficult to do consistently.

Clinically, ferumoxytol can be administered and DARC-MRL performed on an "as needed" basis only when significant or potentially confounding veins are seen after intracutaneous gadolinium injection. Alternatively, the simplicity and efficiency of administering ferumoxytol prior to intracutaneous gadolinium is attractive.

It is interesting to note that measured ferumoxytol r2* in plasma was approximately 50% greater than the r2 reported in the literature (120 mM$^{-1}$ sec$^{-1}$ vs. 83 mM$^{-1}$ sec$^{-1}$). The addition of red blood cells, however, has further profound effects on R2* relaxivity. For illustrative purposes, a linear estimate of R2* vs. ferumoxytol concentration yields a "pseudo"-r2*$_{blood}$ of approximately 580 mM$^{-1}$ sec$^{-1}$, or nearly 5 times that of plasma. This dramatic increase in blood R2* presumably relates to the compartmentalization of USPIO outside of red blood cells, creating distinct intra- and extra-cellular water compartments with subsequent large local magnetic field gradients that cause significant signal decay. It is this profound R2* lengthening in blood that allows complete suppression of vascular structures in ferumoxytol-containing blood using gradient echo imaging, as R2* causes signal decay as $e^{-TE \cdot R2*}$.

Measured R2* of ferumoxtyol was independent of magnetic field strength. Previous reports have shown similar r2 field-independence due to magnetization saturation in superparamagentic iron agents. This makes the DARC technique equally effective at 1.5 T and 3 T. DARC-MRL utilizes the extremely high R2* relaxivity of ferumoxytol in blood to suppress vasculature at relatively low concentrations through only modest increase of TE. Irrespective of any increased R1, such as occurs when gadolinium coexists in venous structures, at long TE the R2*-induced signal loss overwhelms any Gd-related R1 signal increase.

One important benefit of using intravascular ferumoxytol is that with a standard "shortest" TE combination, the increased R1 signal enhancement overcomes the R2*-related signal decay and there is sufficient intravascular signal to provide an excellent quality T1-weighted vascular map—something potentially useful for evaluating veins as well as finding coexistent venous anomalies or thrombosis. As an additional potential benefit of using ferumoxytol, an arterial first pass CE-MRA can be performed immediately following IV injection if desired.

The modified Dixon reconstruction effectively suppresses fat signal in the images, even using lengthened TE for DARC imaging. Provided the echoes are separated by approximately 180° water-fat chemical shift (1.15 ms at 3 T, or 2.3 ms at 1.5 T), the water/fat separation appears to work well. In addition, it is desirable to suppress all veins so they do not mimic enhancing lymphatics. This means the ferumoxytol must be distributed throughout all veins. Occasionally, small segments of veins may not completely suppress after initial injection of ferumoxytol. This is likely due to slow or stagnant blood flow. In these cases, manual massage of the affected limb and/or asking the patient to "wiggle" their extremity or contract their muscles in some way increases flow and further distributes the ferumoxytol, eliminating the residual venous signal.

Similar to suppression of veins in MRL, DARC imaging could in theory suppress blood pool signal in other imaging applications as well. DARC imaging can also be used in a similar way for vessel wall imaging and myocardial viability imaging. Both applications benefit from post-Gd imaging with vascular suppression.

Conclusion

An MR imaging technique (DARC) was developed that utilizes i.v. ferumoxytol and extended-echo mDixon to suppress blood-pool signal. The technique provides fat-suppressed, high resolution 3D images that can eliminate any gadolinium-related vascular enhancement. We have demonstrated the technique as applied to MR Lymphangiography, where a conventional Gd-based contrast agent is injected intracutaneously and enhances signal from lymphatic channels and veins, the latter confounding identification of lymphatics. The DARC technique effectively suppresses signal from veins and allows identification and localization of lymphatic channels.

Example 2

MRI Using Ablavar (Gd-Containing) Suppression Agent

MR signal intensity was measured using an mDixon sequence with six different echo time pairs, as indicated in FIG. 6. Six in vitro whole venous blood samples each contained a different concentration (0, 2, 4, 6, 8, and 12 mM) of gadofosveset trisodium (Ablavar). For long echo time pairs (e.g., 11.5 ms/12.7 ms), the signal intensity decreased rapidly with Ablavar concentration greater than about 4 mM. At 12 mM, the signal intensity was below that of pure blood even for echo times as short as 6.9 ms/8.1 ms.

In this example, relatively high concentrations of Ablavar shorten the T2* of water and will suppress signal at longer echo times. While no "contrast agent" (e.g., having a smaller r2*) is included in the samples tested, the presence of such a contrast agent would have little effect (due to low concentration of contrast agent in blood). Thus, Ablavar is a potential vascular suppression agent because it is confined to the vascular compartment.

These results indicate that Ablavar (or other Gd-based blood-pool agents with appropriate r2*) can be used as a blood-pool, MRI suppression agent in accordance with embodiments disclosed herein.

Example 3

MRI Scar Imaging Using Feraheme Suppression Agent

In late gadolinium enhanced imaging of a myocardial scar, often scar, particularly subendocardial scar (FIG. 7a, solid arrow) is difficult to differentiate from the left ventricular blood (FIG. 7a, hollow arrow). In this case, both scar and blood contain Gd contrast agent and appear bright. With the addition of ferumoxytol (FIG. 7b), the blood pool (FIG. 7b, hollow arrow) signal intensity is suppressed compared to background tissue, and the contrast between blood pool and myocardial scar is heightened.

This result demonstrates that the use of MRI suppression agents, as disclosed herein, can be used to suppress MR signal in any applicable technique where vascular signal suppression is desirable.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of producing magnetic resonance imaging (MRI) image of a part of a subject's lymphatic system, comprising
    administering to the subject intracutaneously or subcutaneously a Gd(III) MRI contrast agent having a second r2*;
    administering to the subject intravenously a blood pool MRI suppression agent having a first r2*, wherein the first r2* is greater than the second r2*; and
    producing an MRI image of a part of the lymphatic system with suppressed vascular structures by performing MRI imaging with T2*-weighting, performed at a long echo time (TE), such that a signal related to the MRI suppression agent is suppressed and a remaining signal related to the MRI contrast agent is not suppressed.

2. The method of claim 1, wherein the MRI contrast agent is selected from the group consisting of Gadopentate dimeglumine (Magnevist), Gadobutrol (Gadavist, Gadovist), Gadoteridol (ProHance), Gadobenate dimeglumine (MultiHance), Gadodiamide (Omniscan), Gadoversetamide (OptiMARK), Gadoteric acid (Dotarem), Gadoxetate disodium (Eovist, Primovist), and Gadofesveset trisodium (Ablavar).

3. The method of claim 1, wherein the MRI contrast agent is not a blood pool agent.

4. The method of claim 1, wherein the blood pool MRI suppression agent is selected from the group consisting of an ultrasmall superparamagnetic iron oxide (USPIO) and a gadolinium-containing blood pool agent.

5. The method of claim 1, wherein MRI imaging comprises applying a magnetic field of about 0.5 T to about 7.0 T.

6. The method of claim 1, wherein the method comprises MRI imaging in a location wherein the MRI suppression agent is resident by utilizing T2* weighting at which signal related to the MRI suppression agent is suppressed while a signal due to the MRI contrast agent is present.

7. The method of claim 1, wherein the long TE is from 3 ms to 30 ms.

8. The method of claim 1, wherein the MRI contrast agent is injected intracutaneously into the soft tissues of feet or hands of the subject.

9. The method of claim 1, wherein the step of administering blood pool MRI suppression agent is performed after the step of administering the MRI contrast agent.

10. The method of claim 1, wherein the step of administering the blood pool MRI suppression agent is performed prior to the step of administering the MRI contrast agent.

11. The method of claim 1, wherein the step of administering the blood pool MRI suppression agent is performed concurrently with the step of administering the MRI contrast agent.

12. The method of claim 8, wherein the soft tissues of hands or feet of the subject are web spaces of hands or feet of the subject.

* * * * *